US010577615B2

(12) United States Patent
Liu et al.

(10) Patent No.: US 10,577,615 B2
(45) Date of Patent: Mar. 3, 2020

(54) **GENETICALLY ENGINEERED *CANDIDA UTILIS* CAPABLE OF DEGRADING AND UTILIZING KITCHEN WASTE AND CONSTRUCTION METHOD THEREFOR**

(71) Applicant: GUANGDONG RECYCLEAN LOW-CARBON TECHNOLOGY CO., LTD., Guangzhou, Guangdong (CN)

(72) Inventors: ZeHuan Liu, Guangzhou (CN); JiangHai Lin, Guangdong (CN); Shuai Li, Guangdong (CN)

( * ) Notice: Subject to any disclaimer, the term of this patent is extended or adjusted under 35 U.S.C. 154(b) by 0 days.

(21) Appl. No.: 16/449,858

(22) Filed: Jun. 24, 2019

(65) Prior Publication Data

US 2019/0309315 A1 Oct. 10, 2019

Related U.S. Application Data

(63) Continuation of application No. PCT/CN2017/091532, filed on Jul. 3, 2017.

(30) Foreign Application Priority Data

Dec. 19, 2016 (CN) .......................... 2016 1 1176709

(51) Int. Cl.

| | |
|---|---|
| ***C12N 9/62*** | (2006.01) |
| ***C12P 7/08*** | (2006.01) |
| ***C12N 15/81*** | (2006.01) |
| ***C12N 9/26*** | (2006.01) |
| ***C12N 9/34*** | (2006.01) |
| ***C12N 9/30*** | (2006.01) |

(52) U.S. Cl.

CPC ........... *C12N 15/815* (2013.01); *C12N 9/242* (2013.01); *C12N 9/2414* (2013.01); *C12N 9/2428* (2013.01); *C12N 9/62* (2013.01); *C12P 7/08* (2013.01); *C12Y 302/01001* (2013.01); *C12Y 302/01003* (2013.01); *C12N 2800/102* (2013.01); *C12N 2800/22* (2013.01)

(58) Field of Classification Search

None

See application file for complete search history.

(56) References Cited

FOREIGN PATENT DOCUMENTS

| | | | |
|---|---|---|---|
| BR | 102014028897 | A2 | 9/2016 |
| CN | 103725624 | A | 4/2014 |
| CN | 106701606 | A | 5/2017 |
| JP | 2016-015892 | A | 2/2016 |

OTHER PUBLICATIONS

International Search Report Issued in Patent Application No. PCT/CN2017/091532 dated Oct. 11, 2017.

Written Opinion Issued in Patent Application No. PCT/CN2017/091532 dated Oct. 11, 2017.

English Translation of Yang, Honglan, et al., "Environmental Preliminary Report of Research on Expression System in a kind of Candida Utilis", Xinjiang Agricultural Sciences, Mar. 31, 2008, vol. 45(3), ISSN: 1001-4330, pp. 462-466.

*Primary Examiner* — Padmavathi Baskar

(74) *Attorney, Agent, or Firm* — Pearne & Gordon LLP

(57) ABSTRACT

Provided is a genetically engineered *Candida utilis* capable of degrading and utilizing kitchen waste. The genetically engineered *Candida utilis* is obtained by using a *Candida utilis* multigene co-expression vector to integrate alpha-amylase, glucoamylase and acid protease genes into the *Candida utilis* genome and to correctly express such three enzymes.

4 Claims, 6 Drawing Sheets

Specification includes a Sequence Listing.

SEQUENCE LISTING

```
<160> NUMBER OF SEQ ID NOS: 5

<210> SEQ ID NO 1
<211> LENGTH: 2490
<212> TYPE: DNA
<213> ORGANISM: Artificial Sequence
<220> FEATURE:
<223> OTHER INFORMATION: Synthetic construct alpha-amylase gene

<400> SEQUENCE: 1

ggatccacga tgatggttgc ttggtggtct ttgttcttgt acggtttgca agttgctgct     60

ccagctttgg ctgctacccc agctgattgg agatctcaat ctatctactt cttgttgacc    120

gatagattcg ctagaaccga tggttctacc accgctacct gtaacaccgc tgatcaaaag    180

tactgtggtg gtacctggca aggtatcatc gataagttgg attacatcca aggtatgggt    240

ttcaccgcta tctggatcac cccagttacc gctcaattgc cacaaaccac cgcttacggt    300

gatgcttacc acggttactg gcaacaagat atctactctt tgaacgagaa ctacggtacc    360

gctgatgatt tgaaggcttt gtcttctgct ttgcacgaga gaggtatgta cttgatggtt    420

gatgttgttg ctaaccacat gggttacgat ggtgctggtt cttctgttga ttactctgtt    480

ttcaagccat tctcttctca agattacttc cacccattct gtttcatcca aaactacgag    540

gatcaaaccc aagttgagga ttgttggttg ggtgataaca ccgtttcttt gccagatttg    600

gataccacca aggatgttgt taagaacgag tggtacgatt gggttggttc tttggtttct    660

aactactcta tcgatggttt gagaatcgat accgttaagc acgttcaaaa ggatttctgg    720

ccaggttaca acaaggctgc tggtgtttac tgtatcggtg aggttttgga tggtgatcca    780

gcttacacct gtccatacca aaacgttatg gatggtgttt tgaactaccc aatctactac    840

ccattgttga acgctttcaa gtctacctct ggttctatgg atgatttgta caacatgatc    900

aacaccgtta agtctgattg tccagattct accttgttgg gtaccttcgt tgagaaccac    960

gataacccaa gattcgcttc ttacaccaac gatatcgctt tggctaagaa cgttgctgct   1020

ttcatcatct tgaacgatgg tatcccaatc atctacgctg gtcaagagca acactacgct   1080

ggtggtaacg atccagctaa cagagaggct acctggttgt ctggttaccc aaccgattct   1140

gagttgtaca agttgatcgc ttctgctaac gctatcagaa actacgctat ctctaaggat   1200

accggtttcg ttacctacaa gaactggcca atctacaagg atgataccac catcgctatg   1260

agaaagggta ccgatggttc tcaaatcgtt accatcttgt ctaacaaggg tgcttctggt   1320

gattcttaca ccttgtcttt gtctggtgct ggttacaccg ctggtcaaca attgaccgag   1380

gttatcggtt gtaccaccgt taccgttggt tctgatggta acgttccagt tccaatggct   1440

ggtggtttgc caagagtttt gtacccaacc gagaagttgg ctggttctaa gatctgttct   1500
```

-continued

```
tcttctggtg gtggtggctc gagcgctaag tcttctttca tctctaccac caccaccgat   1560

ttgacctcta tcaacacctc tgcttactct accggttcta tctctaccgt tgagaccggt   1620

aacagaacca cctctgaggt tatctctcac gttgttacca cctctaccaa gttgtctcca   1680

accgctacca cctctttgac catcgctcaa acctctatct actctaccga ttctaacatc   1740

accgttggta ccgatatcca caccacctct gaggttatct ctgatgttga gaccatctcc   1800

agagagaccg cttctaccgt tgttgctgct ccaacctcta ccaccggttg gaccggtgct   1860

atgaacacct acatctctca attcacctct tcttctttcg ctaccatcaa ctctacccca   1920

atcatctctt cttctgctgt tttcgagacc tctgatgctt ctatcgttaa cgttcacacc   1980

gagaacatca ccaacaccgc tgctgttcca tctgaggagc caaccttcgt taacgctacc   2040

agaaactctt tgaactcttt ctgttcttct aagcaaccat cttctccatc ttcttacacc   2100

tcttctccat tggtttcttc tttgtctgtt tctaagacct tgttgtctac ctctttcacc   2160

ccatctgttc caacctctaa cacctacatc aagaccaaga acaccggtta cttcgagcac   2220

accgctttga ccacctcttc tgttggtttg aactctttct ctgagaccgc tgtttcttct   2280

caaggtacca agatcgatac cttcttggtt tcttctttga tcgcttaccc atcttctgct   2340

tctggttctc aattgtctgg tatccaacaa aacttcacct ctacctcttt gatgatctct   2400

acctacgagg gtaaggcttc tatcttcttc tctgctgagt tgggttctat catcttcttg   2460

ttgttgtctt acttgttgtt ctgaactagt                                    2490
```

<210> SEQ ID NO 2
<211> LENGTH: 2913
<212> TYPE: DNA
<213> ORGANISM: Artificial Sequence
<220> FEATURE:
<223> OTHER INFORMATION: Synthetic construct glucoamylase gene

<400> SEQUENCE: 2

```
ggatccacga tgtctttcag atctttgttg gctttgtctg gtttggtttg taccggtttg     60

gctaacgtta tctctaagag agctaccttg gattcttggt tgtctaacga ggctaccgtt    120

gctagaaccg ctatcttgaa caacatcggt gctgatggtg cttgggtttc tggtgctgat    180

tctggtatcg ttgttgcttc tccatctacc gataacccag attacttcta cacctggacc    240

agagattctg gtttggtttt gaagaccttg gttgatttgt tcagaaacgg tgatacctct    300

ttgttgtcta ccatcgagaa ctacatctct gctcaagcta tcgttcaagg tatctctaac    360

ccatctggtg atttgtcttc tggtgctggt ttgggtgagc caaagttcaa cgttgatgag    420

accgcttaca ccggttcttg ggtagacca caaagagatg gtccagcttt gagagctacc    480

gctatgatcg gtttcggtca atggttgttg gataacggtt acacctctac cgctaccgat    540

atcgtttggc cattggttag aaacgatttg tcttacgttg ctcaatactg gaaccaaacc    600

ggttacgatt tgtgggagga ggttaacggt tcttctttct tcaccatcgc tgttcaacac    660

agagctttgg ttgagggttc tgctttcgct accgctgttg gttcttcttg ttcttggtgt    720

gattctcaag ctccagagat cttgtgttac ttgcaatctt tctggaccgg ttctttcatc    780

ttggctaact tcgattcttc cagatctggt aaggatgcta acaccttgtt gggttctatc    840

cacaccttcg atccagaggc tgcttgtgat gattctacct tccaaccatg ttctccaaga    900

gctttggcta accacaagga ggttgttgat tctttcagat ctatctacac cttgaacgat    960

ggtttgtctg attctgaggc tgttgctgtt ggtagatacc cagaggatac ctactacaac   1020

ggtaacccat ggttcttgtg taccttggct gctgctgagc aattgtacga tgctttgtac   1080
```

-continued caatgggata agcaaggttc tttggaggtt accgatgttt ctttggattt cttcaaggct 1140
ttgtactctg atgctgctac cggtacctac tcttcttctt cttctaccta ctcttctatc 1200
gttgatgctg ttaagacctt cgctgatggt ttcgtttcta tcgttgagac ccacgctgct 1260
tctaacggtt ctatgtctga gcaatacgat aagtctgatg gtgagcaatt gtctgctaga 1320
gatttgacct ggtcttacgc tgctttgttg accgctaaca acagaagaaa ctctgttgtt 1380
ccagcttctt ggggtgagac ctctgcttct tctgttccag gtacctgtgc tgctacctct 1440
gctatcggta cctactcttc tgttaccgtt acctcttggc catctatcgt tgctaccggt 1500
ggtaccacca ccaccgctac cccaaccggt tctggttctg ttacctctac ctctaagacc 1560
accgctaccg cttctaagac ctctacctct acctcttcta cctcttgtac caccccaacc 1620
gctgttgctg ttaccttcga tttgaccgct accaccacct acggtgagaa catctacttg 1680
gttggttcta tctctcaatt gggtgattgg gagacctctg atggtatcgc tttgtctgct 1740
gataagtaca cctcttctga tccattgtgg tacgttaccg ttaccttgcc agctggtgag 1800
tctttcgagt acaagttcat cagaatcgag tctgatgatt ctgttgagtg ggagtctgat 1860
ccaaacagag agtacaccgt tccacaagct tgtggtacct ctaccgctac cgttaccgat 1920
acctggagag gtggtggtgg ctcgagcgct aagtcttctt tcatctctac caccaccacc 1980
gatttgacct ctatcaacac ctctgcttac tctaccggtt ctatctctac cgttgagacc 2040
ggtaacagaa ccacctctga ggttatctct cacgttgtta ccacctctac caagttgtct 2100
ccaaccgcta ccacctcttt gaccatcgct caaacctcta tctactctac cgattctaac 2160
atcaccgttg gtaccgatat ccacaccacc tctgaggtta tctctgatgt tgagaccatc 2220
tccagagaga ccgcttctac cgttgttgct gctccaacct ctaccaccgg ttggaccggt 2280
gctatgaaca cctacatctc tcaattcacc tcttcttctt tcgctaccat caactctacc 2340
ccaatcatct cttcttctgc tgttttcgag acctctgatg cttctatcgt taacgttcac 2400
accgagaaca tcaccaacac cgctgctgtt ccatctgagg agccaacctt cgttaacgct 2460
accagaaact ctttgaactc tttctgttct tctaagcaac catcttctcc atcttcttac 2520
acctcttctc cattggtttc ttctttgtct gtttctaaga ccttgttgtc tacctctttc 2580
accccatctg ttccaacctc taacacctac atcaagacca agaacaccgg ttacttcgag 2640
cacaccgctt tgaccacctc ttctgttggt ttgaactctt tctctgagac cgctgtttct 2700
tctcaaggta ccaagatcga taccttcttg gtttcttctt tgatcgctta cccatcttct 2760
gcttctggtt ctcaattgtc tggtatccaa caaaacttca cctctacctc tttgatgatc 2820
tctacctacg agggtaaggc ttctatcttc ttctctgctg agttgggttc tatcatcttc 2880
ttgttgttgt cttacttgtt gttctgaact agt 2913

<210> SEQ ID NO 3
<211> LENGTH: 1200
<212> TYPE: DNA
<213> ORGANISM: Artificial Sequence
<220> FEATURE:
<223> OTHER INFORMATION: Synthetic construct acid protease gene

<400> SEQUENCE: 3
ggatccacta tggttgtttt ctctaagacc gctgctttgg ttttgggttt gtcttctgct 60
gtttctgctg ctccagctcc aaccagaaag ggtttcacca tcaaccaaat cgctagacca 120
gctaacaaga ccagaaccat caacttgcca ggtatgtacg ctagatcttt ggctaagttc 180

-continued

```
ggtggtaccg ttccacaatc tgttaaggag gctgcttcta agggttctgc tgttaccacc    240

ccacaaaaca acgatgagga gtacttgacc ccagttaccg ttggtaagtc taccttgcac    300

ttggatttcg ataccggttc tgctgatttg tgggttttct ctgatgagtt gccatcttct    360

gagcaaaccg gtcacgattt gtacacccca tcttcttctg ctaccaagtt gtctggttac    420

acctgggata tctcttacgg tgatggttct tctgcttctg gtgatgttta cagagatacc    480

gttaccgttg gtggtgttac caccaacaag caagctgttg aggctgcttc taagatctct    540

tctgagttcg ttcaaaacac cgctaacgat ggtttgttgg gtttggcttt ctcttctatc    600

aacaccgttc aaccaaaggc tcaaaccacc ttcttcgata ccgttaagtc tcaattggat    660

tctccattgt tcgctgttca attgaagcac gatgctccag gtgtttacga tttcggttac    720

atcgatgatt ctaagtacac cggttctatc acctacaccg atgctgattc ttctcaaggt    780

tactggggtt tctctaccga tggttactct atcggtgatg gttcttcttc ttcttctggt    840

ttctctgcta tcgctgatac cggtaccacc ttgatcttgt tggatgatga gatcgtttct    900

gcttactacg agcaagtttc tggtgctcaa gagtctgagg aggctggtgg ttacgttttc    960

tcttgttcta ccaacccacc agatttcacc gttgttatcg gtgattacaa ggctgttgtt   1020

ccaggtaagt acatcaacta cgctccaatc tctaccggtt cttctacctg tttcggtggt   1080

atccaatcta actctggttt gggtttgtct atcttgggtg atgttttctt gaagtctcaa   1140

tacgttgttt tcaactctga gggtccaaag ttgggtttcg ctgctcaagc ttgaactagt   1200


<210> SEQ ID NO 4
<211> LENGTH: 28
<212> TYPE: DNA
<213> ORGANISM: Artificial Sequence
<220> FEATURE:
<223> OTHER INFORMATION: Synthetic construct primer CuGAP-F

<400> SEQUENCE: 4

gctagcttac agcgagcact caaatctg                                         28


<210> SEQ ID NO 5
<211> LENGTH: 36
<212> TYPE: DNA
<213> ORGANISM: Artificial Sequence
<220> FEATURE:
<223> OTHER INFORMATION: Synthetic construct primer CuGAP-R

<400> SEQUENCE: 5

ggatcctatg ttgtttgtaa gtgtgttttg tatctg                                36
```

GENETICALLY ENGINEERED *CANDIDA UTILIS* CAPABLE OF DEGRADING AND UTILIZING KITCHEN WASTE AND CONSTRUCTION METHOD THEREFOR

CROSS-REFERENCE TO RELATED APPLICATIONS

This application is a continuation of International Appl. PCT/CN2017/091532, filed Jul. 3, 2017, which claims priority of Chinese Patent Appl. No. 201611176709.2, filed Dec. 19, 2016, each of which is hereby incorporated by reference.

TECHNICAL FIELD

The present invention relates to the field of genetic engineering and fermentation engineering, in particular to a genetically engineered *Candida utilis* capable of degrading and utilizing kitchen waste and a construction method therefor.

BACKGROUND ART

Kitchen waste is the food waste and residues of families, dining rooms and food and beverage industry, which is the important component of urban domestic waste. Kitchen waste has a high water content and is rich in nutrient substances, wherein the organic content accounts for over 95% of the dry matter, which is rich in starches, saccharides, proteins and fats, etc. Kitchen waste also contains vitamins and microelements such as nitrogen, phosphorus, sulfur, potassium, calcium and magnesium. The nutrient elements are complete and can be reused by organisms. However, just because kitchen waste has a high water content and is rich in nutrient substances, under normal temperature conditions, microorganisms will use various organics and inorganic salts to rapidly breed and metabolize, so that the kitchen waste will rot and smell, polluting the environment and being very difficult to deal with. The amount of kitchen waste is huge, and in China, the annual amount of kitchen waste is over 60 million tons. However, at present, most of kitchen waste is used to feed pigs, landfills, or even be made to “waste oils”, which cause serious environmental pollution. Only a small part is used reasonably, such as incineration, composting and being made to marsh gas, however, the economic benefits are low. Therefore, finding a way to fully utilize the kitchen waste is an important issue in the treatment of kitchen waste.

Since kitchen waste is rich in organics such as starches, saccharides and proteins, it is an ideal renewable material. Using kitchen waste as the raw material for the production of non-food fuel ethanol is a promising development direction. On the one hand, it can solve the problem of resource utilization of kitchen waste, which can not only turn waste into treasure, and improve economic efficiency, but also solve environmental pollution problems, with enormous social benefits. On the other hand, using kitchen waste as the raw material can solve the problem that the raw material of fuel ethanol production in China right now is mainly based on grain starch, which pushes up the price of food and causes food crisis.

*Candida utilis*, also known as round protein-producing yeast or edible round yeast, is a safe yeast (GRAS, Generally Recognized as Safe) approved by US Food and Drug Administration (FDA), and also a “fungus which can be used for health food” approved by China Food and Drug Administration. *Candida utilis* is an important industrial yeast, and is used for producing a variety of high-value-added biological agents, such as glutathione, RNA, amylase, L-lactic acid and carotenoid. Similar to *Saccharomyces cerevisiae, Candida utilis* can produce ethanol by glucose fermentation and has a comparable sugar alcohol conversion rate to that of *Saccharomyces cerevisiae*. Furthermore, compared with *Saccharomyces cerevisiae, Candida utilis* has the following advantages: (1) *Candida utilis* is Crabtree-negative, and when growing in a glucose-rich medium, its respiration is not inhibited and ethanol is not produced; and it can grow rapidly under a strict aerobic condition; (2) *Candida utilis* has a high fermentation density, and under an effective continuous culture condition, it can achieve a high density culture, wherein the dry weight of cells can reach 92 g/L, which is beneficial to produce the desired products efficiently; (3) *Candida utilis* can use cheap molasses and wood hydrolysate as the nutrient for growth, saving production costs; (4) *Candida utilis* can use pentoses and hexoses as carbon sources at the same time; (5) *Candida utilis* is adaptive to various carbon sources and nitrogen sources (comprising urea and nitric acid), and its protein content and Vitamin B content are higher than those of *Saccharomyces cerevisiae*; (6) its secretory proteome contains no protease, which is conducive to the expression of heterologous proteins as a host strain; and (7) *Candida utilis* is an edible and safe single-cell protein whose products and the fungal cells per se can be directly used as additives in industries of food, pharmaceuticals, and cosmetics without complex separation and purification procedures, thus saving time and labors.

However, *Candida utilis* lacks enzymes for effectively degrading starch into glucose, and degrading proteins into polypeptides and amino acids, so it cannot directly use starch and proteins in kitchen waste as the carbon sources and nitrogen sources to produce ethanol by fermentation. Therefore, for using kitchen waste as the raw material to produce ethanol by fermentation, it is necessary to introduce the genes of enzymes which are capable of degrading starch and proteins into *Candida utilis* by genetic engineering, to compensate for the defect in its ability of degrading kitchen waste. Therefore, the recombinant *Candida utilis* can degrade starch and proteins in kitchen waste into available carbon sources and nitrogen sources using the amylase and protease synthesized itself, thereby realizing the industrial purpose of using the fermentation of kitchen waste for producing ethanol.

SUMMARY OF THE INVENTION

In view of this, the object of the present invention is to overcome the defects in the prior art and to provide a genetically engineered *Candida utilis* capable of degrading and utilizing kitchen waste.

In order to solve the above-mentioned technical problem, the present invention is achieved by using the technical solution as follows:

A method for constructing a genetically engineered *Candida utilis* capable of degrading and utilizing kitchen waste, said genetically engineered *Candida utilis* is constructed by using a *Candida utilis* multigene co-expression vector (pCuIKP) to integrate alpha-amylase (amy), glucoamylase (ga) and acid protease (ap) genes into the *Candida utilis* genome.

In the present invention, the alpha-amylase which is integrated into the *Candida utilis* genome is derived from *Aspergillus oryzae*, and glucoamylase and acid protease are derived from *Aspergillus niger*. Said alpha-amylase and glucoamylase are in surface display expressions; and said acid protease is in a secretory expression.

The DNA sequences of the alpha-amylase, glucoamylase and acid protease of the present invention are redesigned and obtained by an artificial synthesis and according to the codon usage bias of *Candida utilis*, and a 3'-transmembrane region sequence of alpha-agglutinin of *Saccharomyces cerevisiae* is added to each 3'-terminus of the alpha-amylase and the glucoamylase, such that they can be immobilized on the surface of *Candida utilis*, realizing the surface display expressions. The sequence of alpha-agglutinin of *Saccharomyces cerevisiae* used is also codon optimized for the codon usage bias of *Candida utilis*. The sequence of the alpha-amylase is as shown in SEQ ID NO.1; the sequence of the glucoamylase is as shown in SEQ ID NO.2; and the sequence of the acid protease is as shown in SEQ ID NO.3.

The *Candida utilis* multigene co-expression vector (pCuIKP) is obtained by using *Saccharomyces cerevisiae* multigene co-expression vector (pScIKP) as the basis, removing the rDNA sequence from pScIKP, and replacing the phosphoglycerate kinase promoter of *Saccharomyces cerevisiae* in pScIKP with the glyceraldehyde-3-phosphate dehydrogenase promoter of *Candida utilis*. The specific modification steps are as follows:

1) excising the rDNA fragment of pScIKP by using restriction endonucleases XbaI and SacI, and blunting the overhangs obtained after the enzyme digestion by using a single-strand specific endonuclease (S1 nuclease, Takara), then cyclizing the vector by using a DNA ligase to obtain the vector with rDNA deleted;

2) obtaining the DNA fragment of the promoter (CuGAP) of glyceraldehyde-3-phosphate dehydrogenase of *Candida utilis* by PCR amplification; and 3) performing double digestion on CuGAP fragment and the vector obtained by 1) by using restriction endonucleases NheI and BamHI respectively, then ligating CuGAP into the vector to obtain the *Candida utilis* expression vector pCuIKP in which PGK promoter is replaced with CuGAP.

The method for constructing the genetically engineered *Candida utilis* are specifically as follows:

S1: synthesizing respective DNA sequences based on the amino acid sequences of alpha-amylase, glucoamylase and acid protease and according to the codon usage bias of *Candida utilis*, while adding suitable restriction endonuclease recognition sites as follows to both terminuses of these sequences: BamHI and Spa; performing the double digestion on the *Candida utilis* multigene co-expression vector, the *Saccharomyces cerevisiae* multigene co-expression vector, the alpha-amylase gene as shown in SEQ ID NO.1, the glucoamylase gene as shown in SEQ ID NO.2 and the acid protease gene as shown in SEQ ID NO.3 by using restriction endonucleases BamHI and SpeI, and purifying and recovering the desired fragments;

S2: ligating the alpha-amylase gene and the glucoamylase gene into pScIKP respectively by using a DNA ligase, and ligating the acid protease gene into pCuIKP to form 3 recombinant single gene expression vectors;

S3: cleaving the entire alpha-amylase gene expression cassette and glucoamylase gene expression cassette which contain the promoter fragment and the terminator fragment of the vector from the corresponding recombinant single gene expression vector by using a restriction endonuclease, then ligating same one by one into the restriction single gene expression vector which bears the acid protease gene in the form of tandem expression cassettes, thus constructing a three-gene co-expression vector of alpha-amylase, glucoamylase and acid protease; and S4: performing the single digestion on the three-gene co-expression vector constructed above by using the restriction endonuclease SacI, then transforming the product into the *Candida utilis* after linearization and integrating same into the genome, thus obtaining the genetically engineered *Candida utilis* capable of degrading and utilizing kitchen waste.

In step S3, constructing the three-gene co-expression vector comprises the steps as follows:

S11: performing double digestion on the recombinant single gene expression vectors of alpha-amylase and glucoamylase by using restriction endonucleases NheI and XbaI, recovering the entire expression cassettes of the alpha-amylase gene and the glucoamylase gene which bear the promoter and terminator of the vector respectively;

S12: performing enzyme digestion on the recombinant single gene expression vector of acid protease by using the restriction endonuclease NheI, then ligating the glucoamylase gene expression cassette into the recombinant single gene expression vector of acid protease by using the feature of isocaudomers between NheI and XbaI, thus constructing a two-gene expression vector of glucoamylase and acid protease; and S13: performing enzyme digestion on the two-gene expression vector constructed in step S12 by using the restriction endonuclease NheI, then ligating the alpha-amylase gene expression cassette into the two-gene expression vector, thus constructing a three-gene co-expression vector of alpha-amylase, glucoamylase and acid protease.

Compared with the prior art, the present invention has the following beneficial effects: The present invention utilizes *Candida utilis* instead of the *Saccharomyces cerevisiae* commonly used in the ethanol fermentation industry, which has the following advantages: firstly, *Candida utilis* has the same safety as and a similar ethanol fermentation capacity to *Saccharomyces cerevisiae*; secondly, *Candida utilis* can use molasses and wood hydrolysate for growth and can make use of hexose and pentose, having a wider sugar spectrum and higher adaptability than those of *Saccharomyces cerevisiae*; and thirdly, *Candida utilis* is Crabtree-negative, can achieve a higher culture density than that of *Saccharomyces cerevisiae*, and accordingly can harvest more fungal cells during the strain production stage, thus saving the culture time and cost.

The present invention discloses a genetically engineered *Candida utilis*, wherein the alpha-amylase and the glucoamylase are in surface display expressions, and the acid protease is in a secretory expression. Since alpha-amylase and glucoamylase are enzymes necessary for starch degrading, in order to make the genetically engineered strain use starch material in kitchen waste better, it is necessary to inoculate a fermentation strain while introducing an amylase. In the case of secretory expression, the genetically engineered strain per se carry no enzyme and it needs to be scaled up and cultured in advance to produce enough enzymes for degradation, then said strain can be inoculated into kitchen waste, resulting in operational complexity. Furthermore, the inoculation volume is generally 10% of that of the kitchen waste to be treated. For industrial fermentation, this greatly increases the equipment cost required by the preparation of a fermentation strain. On the contrary, in the case of surface display expression, an amylase can be added during the production of the fungus seed, so it can be prepared into an active dry yeast while retaining the amylase activity. Before the degradation of kitchen waste, it only needs a simple activation, then the fungus seed can be inoculated into kitchen waste. The required volume is only 0.05%, which greatly simplifies operation. Furthermore, the fungus seed can be prepared in the form of dry yeast, which is convenient for preservation and is very suitable for industrial application.

DETAILED DESCRIPTION OF EMBODIMENTS

In order to make a person skilled in the art better understand the solution of the present invention, hereafter the present invention will be further described in details in conjunction with accompanying drawings.

Embodiment

The *Candida utilis* used in this embodiment is purchased from Guangdong Culture Collection Center (number: GIM2.176). Vector pScIKP is constructed and deposited by Research Center for Molecular Biology, Jinan University.

I. Construction of *Candida utilis* Expression Vector pCuIKP

1. Perform double digestion for cleaving *Saccharomyces cerevisiae* expression vector pScIKP by using restriction endonucleases XbaI and SacI and excise the *Saccharomyces cerevisiae* rDNA sequence fragment from pScIKP.

2. Excise the overhangs generated by the double digestion in step 1 above by using single-strand specific endonuclease (S1 nuclease, Takara) to obtain the fragments with blunt ends; then cyclize the obtained fragments with blunt ends by using T4 DNA ligase to obtain the vector with rDNA deleted.

3. With reference to the promoter (CuGAP) sequence of glyceraldehyde-3-phosphate dehydrogenase of the *Candida utilis* published by NCBI (Accession: FJ664342), design primers using Primer 3 software, while adding corresponding restriction sites as follows:

```
CuGAP-F:
                                        (SEQ ID NO: 4)
5'-GCTAGCTTACAGCGAGCACTCAAATCTG-3',
```

wherein the underlined sequence corresponds to an NheI site, and

```
CuGAP-R:
                                        (SEQ ID NO: 5)
5'-GGATCCTATGTTGTTTGTAAGTGTGTTTTGTATCTG-3',
```

wherein the underlined sequence corresponds to a BamHI site, wherein the genomic DNA of *Candida utilis* GIM2.176 is used as the template to obtain CuGAP promoter fragment by PCR amplification, then ligating the PCR amplification product to pMD18-T vector (Takara) and performing verification by sequencing.

PCR reaction conditions are as follows:

| | |
|---|---|
| 94° C. | 5 min |
| 98° C. | 15 s |
| 55° C. | 30 s |
| 72° C. | 1 min |
| 30 cycles | |
| 72° C. | 10 min |

Figure 1:
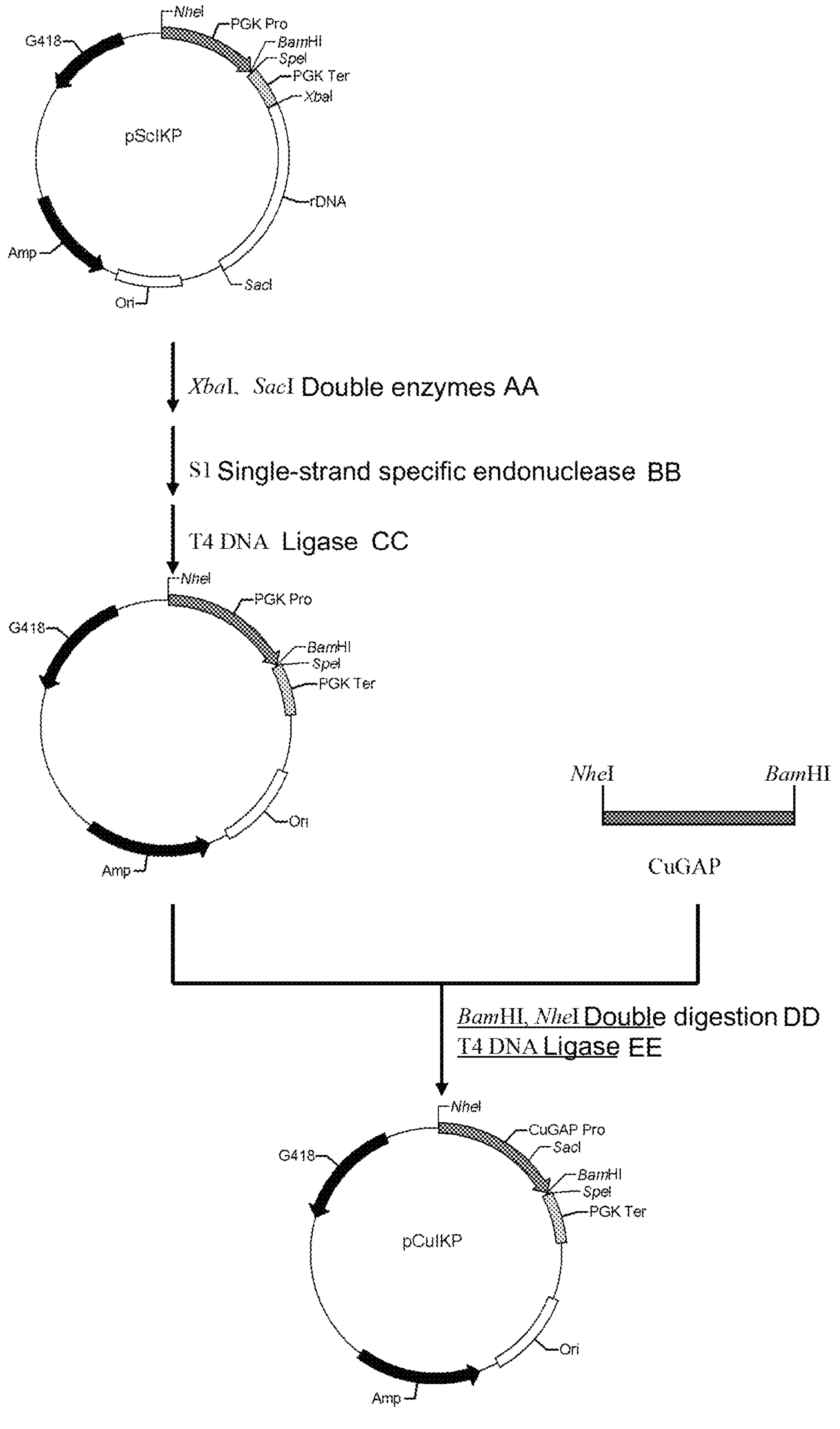
FIG. 1 is the construction of *Candida utilis* expression vector pCuIKP.

4. Perform double digestions, with restriction endonucleases NheI and BamHI, on the vector obtained above in step 2 and on the CuGAP fragment verified via sequencing obtained above by step 3; then ligate the enzyme digested CuGAP to the vector by using a T4 DNA ligase, and obtain *Candida utilis* expression vector pCuIKP (as shown in FIG. 1).

II. Constructions of Single-Gene Expression Vectors of Alpha-Amylase, Glucoamylase and Acid Protease 1. According to the amino acid sequences of alpha-amylase gene amy (Accession: XM_001821384) derived from *Aspergillus oryzae*, and of glucoamylase gene ga (Accession: XM_001390493.1) and acid protease gene ap (Accession: XM_001401056.2) derived from *Aspergillus niger* which are published by NCBI, codon optimizations are performed with reference to the codon usage bias of *Candida utilis*, and the optimized DNA sequences (see SEQ.ID 1-3) are synthesized. The anchor sequence at the carboxyl end of alpha-agglutinin of *Saccharomyces cerevisiae* is fused to the alpha-amylase and the glucoamylase respectively to achieve the surface display expressions. The synthesized sequences are cloned to vector pUC57, and are respectively named as pUC57-amy, pUC57-ga and pUC57-ap.

2. Perform double digestions on pScIKP, pCuIKP, pUC57-amy, pUC57-ga and pUC57-ap by using restriction endonucleases BamHI and SpeI, and recover and purify the desired vectors and gene fragments.

Figure 2A:
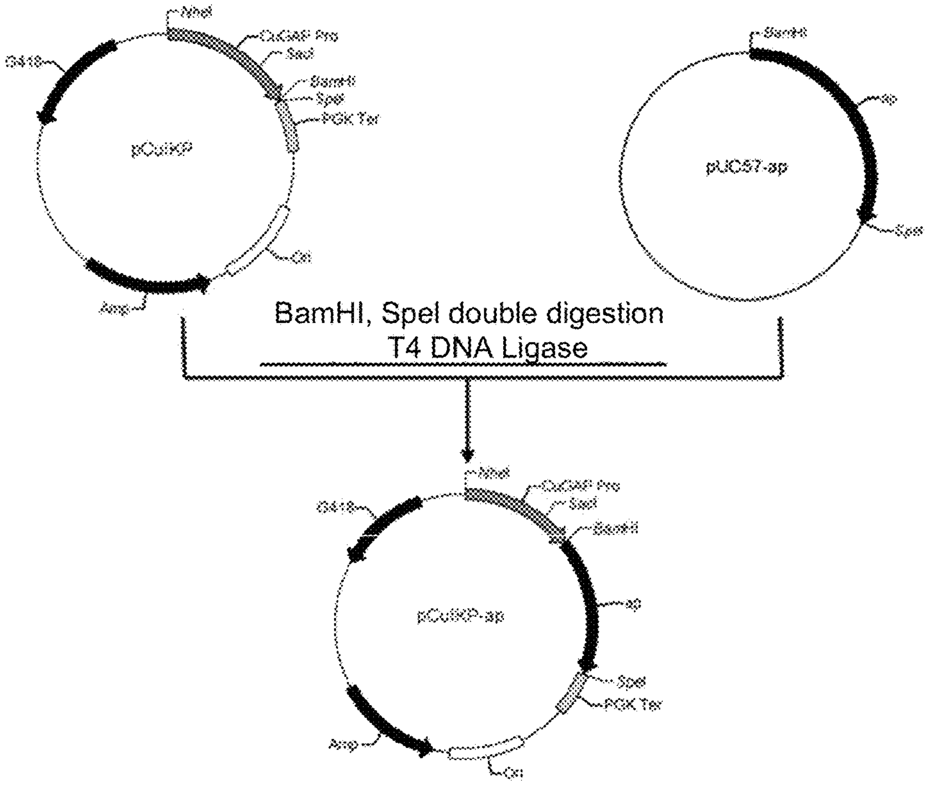
FIG. 2 is the constructions of single-gene expression vectors of alpha-amylase (FIG. 2*b*), glucoamylase (FIG. 2*c*) and acid protease (FIG. 2*a*).

3. Ligate acid protease gene to pCuIKP vector by using a T4 DNA ligase and obtain acid protease single-gene expression vector pCuIKP-ap (as shown in FIG. 2*a*).

Figure 2B:
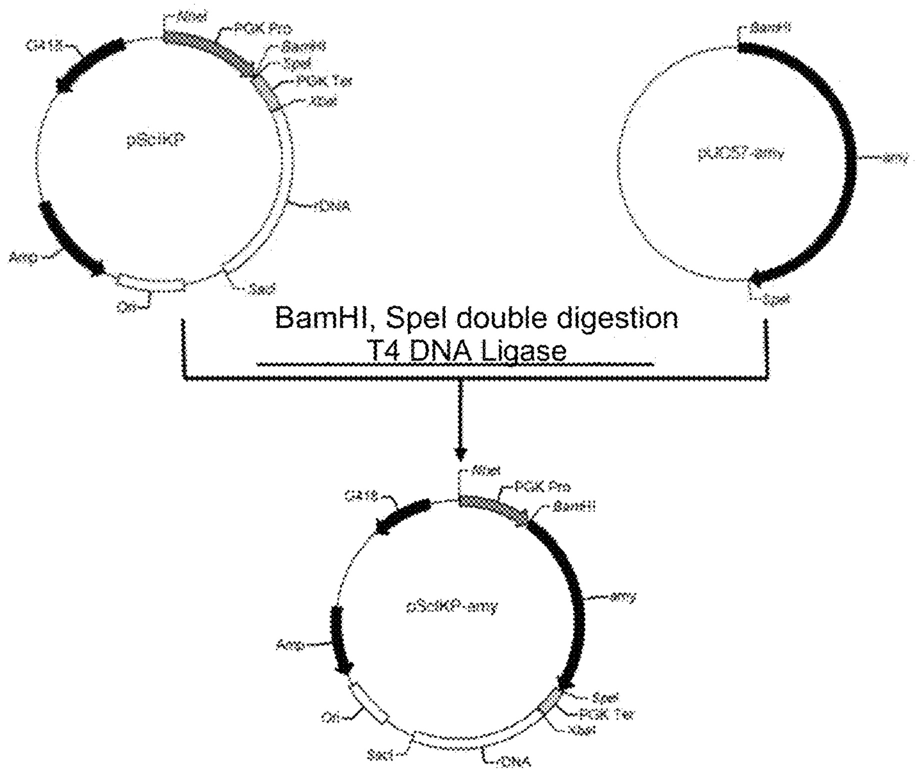

4. Ligate alpha-amylase gene to pScIKP vector by using a T4 DNA ligase and obtain alpha-amylase single-gene expression vector pScIKP-amy (as shown in FIG. 2*b*).

Figure 2C:
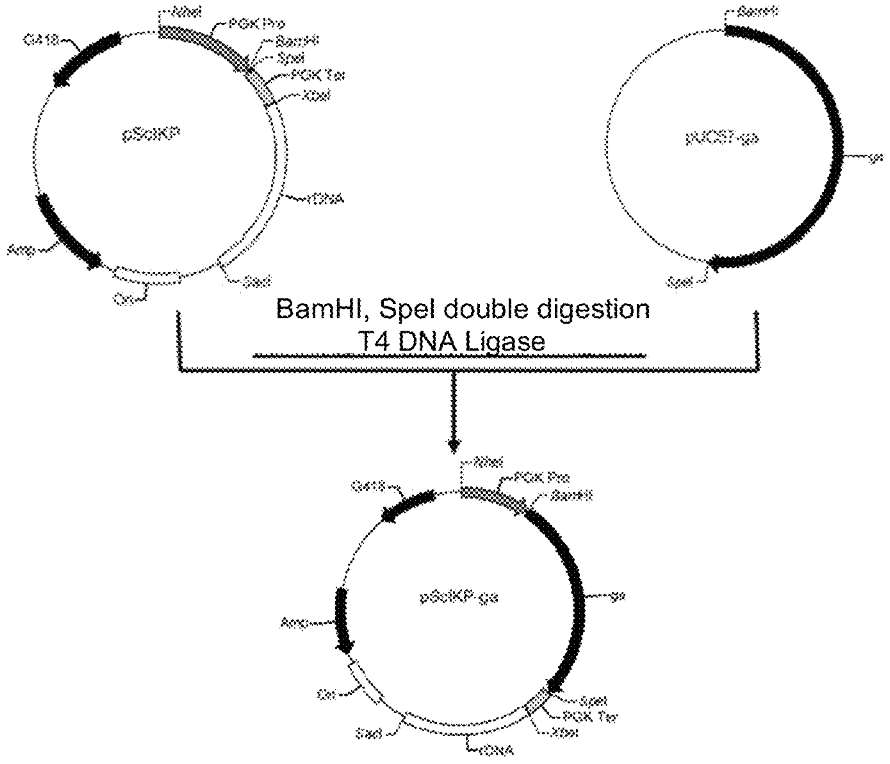

5. Ligate glucoamylase gene to pScIKP vector by using a T4 DNA ligase and obtain glucoamylase single-gene expression vector pScIKP-ga (as shown in FIG. 2*c*).

At this point, the single-gene expression vectors of the three genes are constructed.

III. Construction of the Three-Gene Co-Expression Vector of Alpha-Amylase, Glucoamylase and Acid Protease and Transformation into *Candida utilis*

1. Perform single digestion on pCuIKP-ap by using restriction endonuclease NheI, then dephosphorylate the product after the enzyme digestion, thus obtaining pCuIKP-ap with NheI overhangs.

2. Perform double digestion on pScIKP-ga by using restriction endonucleases NheI and XbaI, then recover the entire expression cassette of glucoamylase gene which has the promoter and terminator of the vector.

3. Make use of the fact that NheI and XbaI are isocaudomers and have the same overhangs and ligate the vector and the expression cassette of glucoamylase gene obtained above in steps 1 and 2 by using a T4 DNA ligase, thus obtaining two-gene expression vector pCuIKP-ga-ap.

4. Perform single digestion on pCuIKP-ga-ap by using restriction endonuclease NheI, then dephosphorylate the product after the enzyme digestion, thus obtaining pCuIKP-ga-ap with NheI overhangs.

5. Perform double digestion on pScIKP-amy by using restriction endonucleases NheI and XbaI, then recover the entire expression cassette of alpha-amylase gene which has the promoter and terminator of the vector.

Figure 3:
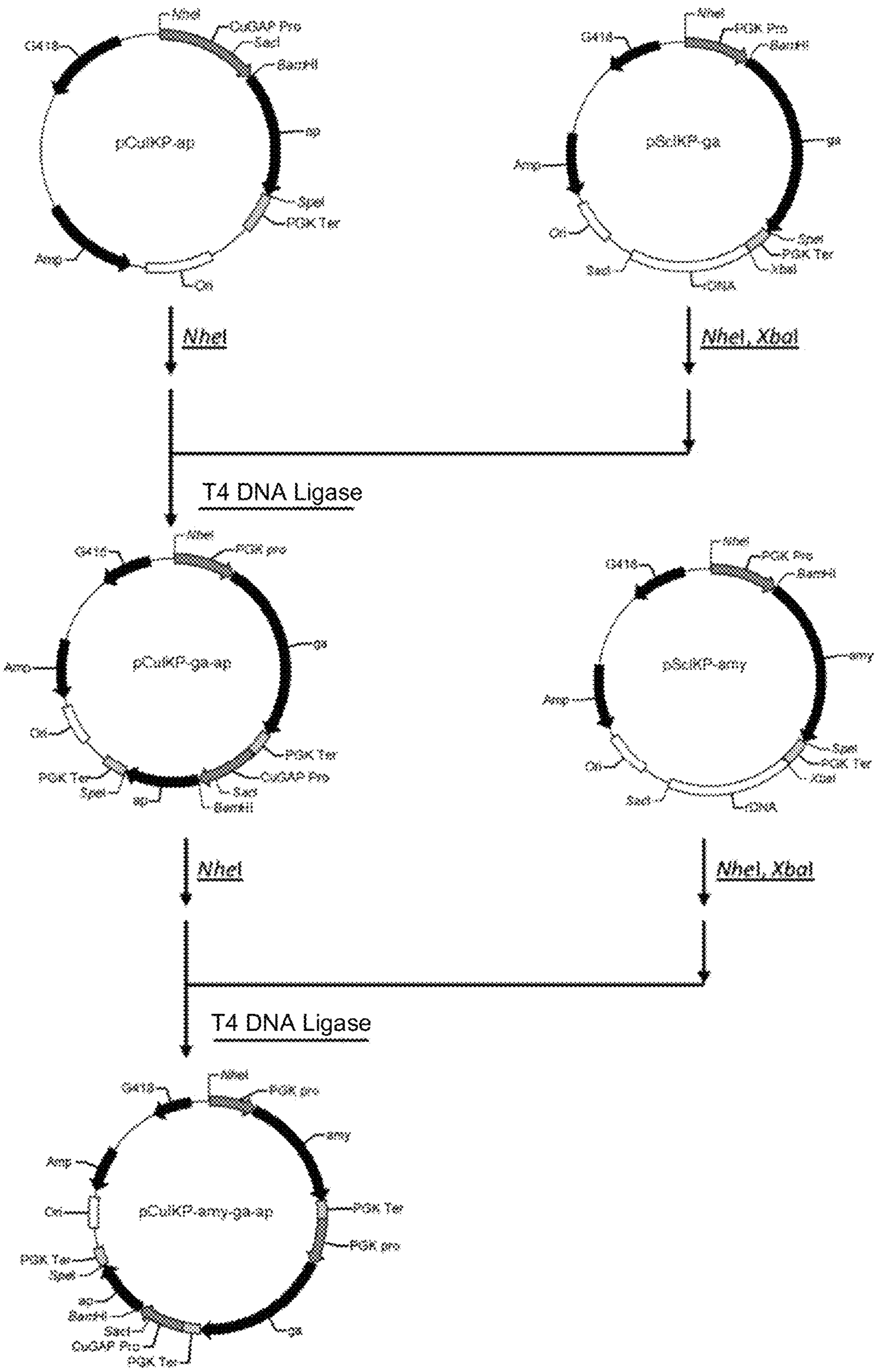
FIG. 3 is the construction of the three-gene co-expression vector of alpha-amylase, glucoamylase and acid protease.

6. Make use of the fact that NheI and XbaI are isocaudomers and have the same overhangs and ligate the vector and expression cassette of alpha-amylase gene obtained above in steps 4 and 5 by using a T4 DNA ligase, thus obtaining three-gene expression vector pCuIKP-amy-ga-ap (as shown in FIG. 3).

7. Linearize the three-gene co-expression vector pCuIKP-amy-ga-ap obtained above in step 6 by using restriction endonuclease SacI, transform same into *Candida utilis* GIM2.176 by electroporation transformation, culture the yeast on YPD agar plate with G418 concentration of 300 μg/ml for 3 to 4 d, then picking the colonies with normal growth, they are the transformants which have been transformed with the above-mentioned recombinant plasmid. Identify the positive transformant by colony PCR, which is the genetically engineered *Candida utilis* capable of degrading and utilizing kitchen waste of the present invention.

IV. Activity Detection of Amylase and Protease Expressed by the Genetically Engineered *Candida utilis*

1. Inoculate the positive genetically engineered *Candida utilis* obtained in "III. Construction of the three-gene co-expression vector of alpha-amylase, glucoamylase and acid protease and transformation into *Candida utilis*" into 5 ml of YPD medium, then culture and activate same at 30° C. and 200 rpm for 24 h.

2. Inoculate the activated strain seeds into 100 ml of YPD medium at the ratio of 1:10, then culture same at 30° C. and 200 rpm for 72 h, and respectively collect fungus cells and supernatant after centrifugation. The fungus cells are used for determining the amylase activity; and the supernatant is used for determining the proteinase activity.

3. Determination of amylase activity: Weigh a certain amount of the fungus cells, add 1 ml of acetic acid-sodium acetate buffer at pH 5.5 to wash twice, and remove residual medium. Then add 1 ml of acetic acid-sodium acetate buffer at pH 5.5 to resuspend the fungus cells, pipet 200 μL of fungus bodies, and add 300 μl of acetic acid-sodium acetate buffer at pH 5.5 thereto, followed by 400 μl of 1% (w/v) soluble starch solution, thoroughly mix same, react same in a water bath at 60° C. for 30 min, and add 100 μl of 0.1 M hydrochloric acid solution cooling in an ice bath to stop the reaction. The total amount of generated reducing sugars is determined by DNS method, and the amylase activity is calculated. The enzyme activity unit is defined as follows: one unit of enzyme activity means the amount of enzyme capable of hydrolyzing starch by 1 g of fungus cells and releasing 1 μmol glucose equivalent of reducing sugars per minute at 60° C., which is represented by U/g.

The result shows that after being cultured for 72 h, the amylase activity of the genetically engineered *Candida utilis* of the present invention is 2477 U/g.

4. Determination of proteinase activity: Pipet 1.0 ml of supernatant, and preheat same in a water bath at 40° C. for 2 min. At the same time, take an appropriate amount of 1% casein solution, and preheat same in water bath at 40° C. for 3 to 5 min, then take 1.0 ml therefrom and add same into the preheated supernatant, immediately start timing, accurately react same in a water bath at 40° C. for 10 min, add 2.0 ml of 0.4 M trichloroacetic acid immediately after the reaction, shake same homogeneously, take same out and stand for 10 min, and filter same. Take 1.0 ml of filtrate, add 5.0 ml of 0.4 M sodium carbonate solution and 1.00 ml of Folin reagent, place same in a water bath at 40° C. for developing over 20 min, take same out and cool same at room temperature. The absorbance of the acid protease is determined by a spectrophotometer at a wavelength of 660 nm using a 10 mm cuvette, and the enzyme activity of the acid protease is calculated according to the L-tyrosine standard curve. The enzyme activity unit is defined as follows: one unit of enzyme activity means the amount of enzyme capable of hydrolyzing casein by 1 g of enzyme solution and releasing 1 microgram tyrosine per minute at 40° C. and pH 3.0, which is represented by U/ml.

The result shows that after being cultured for 72 h, the protease activity of the genetically engineered *Candida utilis* of the present invention is 231 U/ml.

Figure 4:
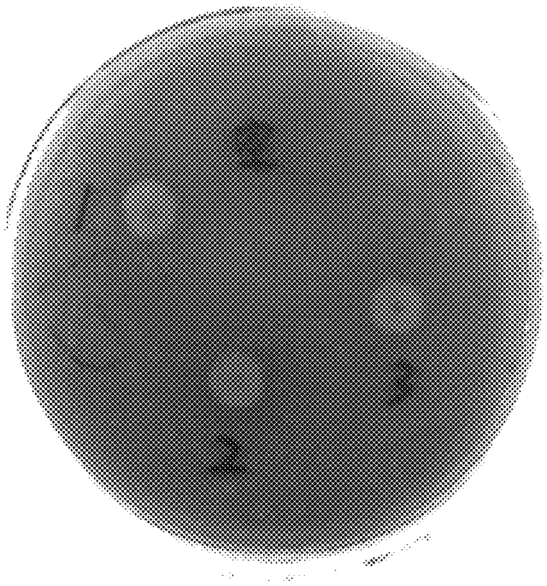
FIG. 4 is the activity detection of amylase expressed by the genetically engineered *Candida utilis*.
Figure 5:
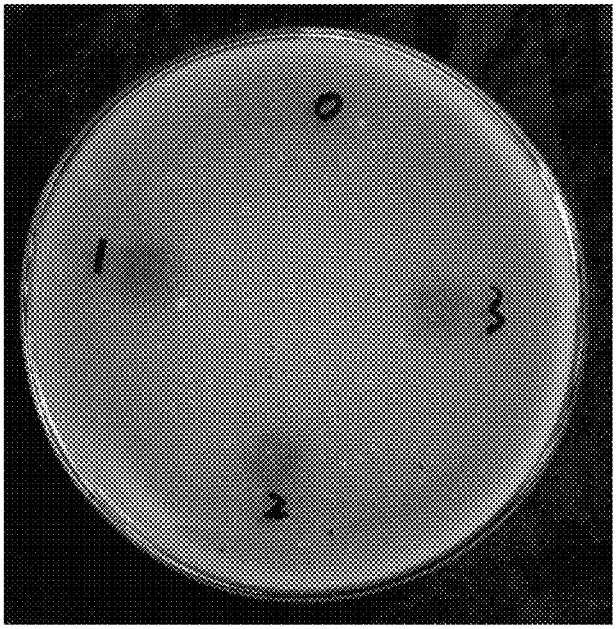
FIG. 5 is the activity detection of protease expressed by the genetically engineered *Candida utilis*.

5. Hydrolysis circle experiment: Inoculate respectively the transformant colony with G418 resistance obtained above in "III. Construction of the three-gene co-expression vector of alpha-amylase, glucoamylase and acid protease and transformation into *Candida utilis*" to YNBS solid medium containing 1% soluble starch and 1% casein (YNB 6.7 g/l, soluble starch 10 g/l and agar powder 15 g/l), then incubate same in an incubator at 30° C. for 3 h, observing the formation of hydrolysis circles respectively (the starch plate must be fumed by iodine in advance). The results are as shown in FIGS. 4 and 5, wherein the transformant can express amylase, glucoamylase and acid protease, so they can degrade and use starch and casein in the medium, thereby forming transparent hydrolysis circles around the colonies.

V. Ethanol Production from the Degradation of Kitchen Waste by the Genetically Engineered *Candida utilis*

Kitchen waste of the present embodiment is collected from post-meal residues of many restaurants in some food street, Guangzhou city. After removing the garbage from the collected kitchen waste, the kitchen waste is pulverized by a garbage pulverizing processor, sterilized at 121° C. for 20 min, and stored at −20° C. for use. Its physical and chemical properties have been determined as follows: the water content is 86.6% and the dry matter content is 13.4%, wherein the protein content is 2.9%, the total sugar content is 4.2%, and the crude fat content is 4.2%, and the pH is 4.2.

Figure 6:
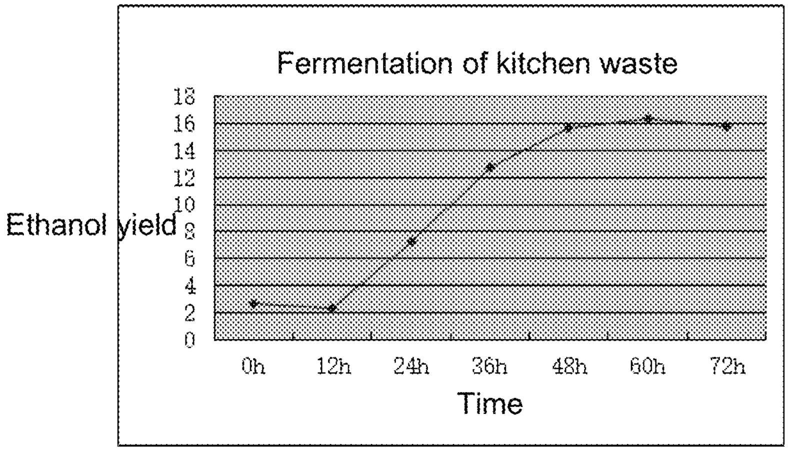
FIG. 6 is the result of ethanol production by using the genetically engineered *Candida utilis* for the fermentation of kitchen waste.

1. Inoculate the positive genetically engineered *Candida utilis* obtained in "III. Construction of the three-gene co-expression vector of alpha-amylase, glucoamylase and acid protease and transformation into *Candida utilis*" into 5 ml of YPD medium, then culture and activate same at 30° C. and 200 rpm for 24 h;

2. Inoculate the activated strain seeds into 200 ml of YPD medium at the ratio of 1:10, then culture same at 30° C. and 200 rpm for 24 h, collect fungus cells by centrifugation, wash same with fresh YPD medium twice, then resuspend the fungus cells with a small amount of YPD medium to obtain a strain seed suspension for fermentation;

3. Weigh 100 g of kitchen waste, inoculate same with the strain seed suspension prepared above in step 2 in an amount of 0.2 gram of fungus cells by dry weight per kg of substrate, stir well and mix homogeneously, then perform the anaerobic fermentation at 30° C. and 200 rpm for 72 h. Sample during the fermentation at the interval of 12 h, detect the ethanol yield of the fermentation broth by HPLC (the result is as shown in FIG. 6). The results show that the peak ethanol production of the recombinant yeast appears around 60 h, the highest ethanol concentration achieves 16.3 g/L, and the sugar alcohol conversion rate achieves 78% of the theoretical value. It can be seen from the above results that the genetically engineered *Candida utilis* capable of degrading and utilizing kitchen waste is constructed in the present invention, which can convert kitchen waste into ethanol, turning kitchen waste into a treasure.

The above-mentioned embodiments are merely specific embodiments in the present invention, giving specifics and details thereof, but should not be understood as limiting the scope of the present patent of invention thereby. It should be noted that a person of ordinary skill in the art could also make several alterations and improvements without departing from the spirit of the present invention and these obvious replacement forms would all fall within the scope of protection of the present invention.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "RUNHE-61081-Sequence-Listing_ST25.txt", created Jun. 24, 2019, file size of 12,288 bytes, is hereby incorporated by reference.

The invention claimed is:

1. A method for constructing a genetically engineered *Candida utilis* capable of degrading and utilizing kitchen waste, wherein the genetically engineered *Candida utilis* expresses a *Candida utilis* multigene co-expression vector that has an alpha-amylase comprising SEQ ID NO: 1, a glucoamylase gene comprising SEQ ID NO: 2, and an acid protease gene comprising SEQ ID NO: 3 and has been integrated into the *Candida utilis* genome, the method comprising steps of:

(1) obtaining the *Candida utilis* multigene co-expression vector by (a) providing a *Saccharomyces cerevisiae* multigene co-expression vector comprising an rDNA sequence, a phosphoglycerate kinase promoter of *Saccharomyces cerevisiae*, and a terminator, (b) removing the rDNA sequence from the *Saccharomyces cerevisiae* multigene co-expression vector, and (c) replacing the phosphoglycerate kinase promoter in the *Saccharomyces cerevisiae* multigene co-expression vector with a glyceraldehyde-3-phosphate dehydrogenase promoter of *Candida utilis*, thereby obtaining the *Candida utilis* multigene co-expression vector;

(2) performing double digestions on the *Candida utilis* multigene co-expression vector, the *Saccharomyces cerevisiae* multigene co-expression vector, the alpha-amylase gene, the glucoamylase gene, and the acid protease gene by using restriction endonucleases to obtain a fragment of DNA comprising the *Candida utilis* multigene co-expression vector, a fragment of DNA comprising the *Saccharomyces cerevisiae* multigene co-expression vector, a fragment of DNA comprising the alpha-amylase gene, a fragment of DNA comprising the glucoamylase gene, and a fragment of DNA comprising the acid protease gene;

(3) purifying and recovering the fragments of DNA comprising the *Candida utilis* multigene co-expression vector, the *Saccharomyces cerevisiae* multigene co-expression vector, the alpha-amylase gene, the glucoamylase gene, and the acid protease gene, respectively;

(4) ligating the fragment of DNA comprising the alpha-amylase gene into the *Saccharomyces cerevisiae* multigene co-expression vector, ligating the fragment of DNA comprising the glucoamylase gene into the fragment of DNA comprising the *Saccharomyces cerevisiae* multigene co-expression vector, and ligating the fragment of DNA comprising the acid protease gene into the fragment of DNA comprising the *Candida utilis* multigene co-expression vector, by using a DNA ligase, to form (i) an alpha-amylase gene expression cassette comprising the phosphoglycerate kinase promoter, the alpha-amylase gene, and the terminator, (ii) a glucoamylase gene expression cassette comprising the phosphoglycerate kinase promoter, the glucoamylase gene, and the terminator, and (iii) an acid protease gene expression cassette comprising the glyceraldehyde-3-phosphate dehydrogenase promoter, the acid protease gene, and the terminator, respectively;

(5) cleaving the alpha-amylase gene expression cassette, the glucoamylase gene expression cassette, and the acid protease gene expression cassette by using one or more restriction endonucleases to form a fragment of DNA comprising the alpha-amylase gene expression cassette, a fragment of DNA comprising the glucoamylase gene expression cassette, and a fragment of DNA comprising the acid protease gene expression cassette, respectively, then ligating the fragment of DNA comprising the alpha-amylase gene expression cassette and the fragment of DNA comprising the glucoamylase gene expression cassette, sequentially into the the fragment of DNA comprising the acid protease gene expression cassette, thus constructing a three-gene co-expression vector of alpha-amylase, glucoamylase, and acid protease;

(6) performing a single digestion on the three-gene co-expression vector by using a restriction endonuclease, and (7) transforming the product into *Candida utilis* thereby integrating the product into the genome, thus obtaining the genetically engineered *Candida utilis* capable of degrading and utilizing kitchen waste.

2. The method for constructing a genetically engineered *Candida utilis* capable of degrading and utilizing kitchen waste according to claim 1, where step (5) is carried out as follows:

the cleaving of the alpha-amylase gene expression cassette and the cleaving of the glucoamylase gene expression cassette are performed as double digestions by using restriction endonucleases;

the fragment of DNA comprising the alpha-amylase gene expression cassette the fragment of DNA comprising the glucoamylase gene expression cassette are recovered;

the cleaving of the fragment of DNA comprising the acid protease gene expression cassette is performed as a single digestion by using a restriction endonuclease;

the recovered fragment of DNA comprising the glucoamylase gene expression cassette is ligated into the fragment of DNA comprising the acid protease gene expression cassette, thus constructing a two-gene co-expression vector of glucoamylase and acid protease;

a single digestion is performed on the two-gene co-expression vector of glucoamylase and acid protease by using a restriction endonuclease to obtain a DNA fragment comprising the two-gene co-expression vector; and the recovered fragment of DNA comprising the alpha-amylase gene expression cassette is ligated into the two-gene co-expression vector, thus constructing the three-gene co-expression vector.

3. The method for constructing a genetically engineered *Candida utilis* capable of degrading and utilizing kitchen waste according to claim 1, wherein the restriction endonucleases in step (2) are BamHI and SpeI; and the restriction endonuclease in step 6 is SacI.

4. The method for constructing a genetically engineered *Candida utilis* capable of degrading and utilizing kitchen waste according to claim 2, wherein the restriction endonucleases used for the cleaving of the alpha-amylase gene expression cassette and the cleaving of the glucoamylase gene expression cassette are NheI and XbaI; the restriction endonuclease used for the cleaving of the fragment of DNA comprising the acid protease gene expression cassette is NheI; and the restriction endonuclease used for performing the single digestion on the two-gene co-expression vector is NheI.

* * * * *